United States Patent [19]

Bosacchi et al.

[11] Patent Number: 4,625,114
[45] Date of Patent: Nov. 25, 1986

[54] METHOD AND APPARATUS FOR NONDESTRUCTIVELY DETERMINING THE CHARACTERISTICS OF A MULTILAYER THIN FILM STRUCTURE

[75] Inventors: Bruno Bosacchi, Montgomery; Robert C. Oehrle, Edgewater Park, both of N.J.

[73] Assignee: AT&T Technologies, Inc., Berkeley Heights, N.J.

[21] Appl. No.: 755,029

[22] Filed: Jul. 15, 1985

[51] Int. Cl.$^4$ .................. G01N 21/41; G01B 11/06
[52] U.S. Cl. ........................ 250/341; 250/353; 356/318
[58] Field of Search .............. 250/353, 341, 358.1; 356/318

[56] References Cited

U.S. PATENT DOCUMENTS

| | | | |
|---|---|---|---|
| 3,436,159 | 4/1969 | Harrick et al. | 356/256 |
| 3,486,829 | 12/1969 | Wilks, Jr. | 356/246 |
| 3,514,183 | 5/1970 | Rabedeau | 350/160 |
| 3,666,358 | 5/1972 | Banks | 353/25 |
| 4,165,155 | 8/1979 | Gordon, II et al. | 350/285 |
| 4,218,143 | 8/1980 | Bottka | 356/445 |

FOREIGN PATENT DOCUMENTS 815484  3/1981  U.S.S.R. ............ 356/381

OTHER PUBLICATIONS

"Study of Physics & Chemistry of Surfaces from Frustrated Total Internal Reflections", by N. J. Harrick, Physical Review Letters, vol. 4, No. 5, pp. 224–226, Mar. 1960.
"Total Internal Reflection & Its Application to Surface Studies", *Annals of New York Academy of Sciences*, pp. 928–929 & 948–949, 1963.
*Internal Reflection Spectroscopy*, by N. J. Harrick, Interscience Publishers (1971), pp. 40–45 & 56–61.
*Internal-Reflection Spectroscopy*", by R. T. Holm & E. D. Palik, Laser Focus, Aug. 1979.
"Resonant Frustrated-Total-Reflection Technique for the Characterization of Thin Films", by B. Bosacchi & R. C. Oehrle, *Applied Optics*, vol. 21, No. 12 (Jun. 15, 1982) pp. 2167–2173.

Primary Examiner—Carolyn E. Fields
Attorney, Agent, or Firm—R. B. Levy

[57] ABSTRACT

Nondestructive characterization of each of the layers ($d_n$) of a multilayer thin film structure (25) is obtained by directing a first beam of radiation (40) into an optical coupler (37) having a base (38) in contact with the surface of the structure (25). The angle of the beam entering the coupler is such that the beam is reflected from the base with an evanescent wave component passing from the coupler and coupling into the multilayer thin film structure as a real beam. The real beam is reflected from the layers of the thin film structure (25) back in the coupler (37) where it combines with the beam (51) reflected from the base and exits the coupler with an intensity related to the characteristics of the structure layers. A servo motor (46) rotates the coupler to scan the first beam therein and a detector (50) detects the intensity of the combined beams exiting the coupler during the scanning thereof by the first beam. A computer (60) compares the detected reflectance intensity sensed by the detector with the reflectance intensity of structures having known characteristics to determine the characteristics of the multilayer thin film structure (25).

11 Claims, 5 Drawing Figures

METHOD AND APPARATUS FOR NONDESTRUCTIVELY DETERMINING THE CHARACTERISTICS OF A MULTILAYER THIN FILM STRUCTURE

TECHNICAL FIELD

This invention relates generally to a method and apparatus for nondestructively determining the characteristics of a multilayer thin film structure. Particularly, the composition and layer thickness of a multilayer thin film structure, such as those used to fabricate electronic integrated circuits, are determined.

BACKGROUND OF THE INVENTION

In the process of fabricating electronic integrated circuit devices, reactants are deposited on the surface of a wafer of semiconducting material to epitaxially grow layers of p- and n-type conducting material thereon to establish the electrical characteristics of the device. In practice, each epitaxially grown layer is usually very thin, on the order of 0.1–10 μm, and has the characteristics of a thin film. For this reason, a semiconductor wafer having a plurality of layers epitaxially grown thereon is often characterized as a multilayer thin film structure.

Controlling the thickness and homogeneity of each epitaxially grown layer during the fabrication process is essential. Variations in the thickness and homogeneity of each layer cause deviations in the electrical characteristics of the resultant device which are undesirable. Therefore, a precise knowledge of the thickness and homogeneity of each layer is required if the fabrication process is to be carried out correctly.

In the past, measurements of the thickness of each layer of an integrated circuit device have been accomplished by viewing a cross section of the device under a scanning electron microscope. When the device is viewed under such a microscope, each layer can be observed quite clearly, allowing the thickness thereof to be determined very accurately. However cross sectioning the device renders it useless for its intended purpose.

For a structure comprised of an energy absorbing substrate having a single thin film layer thereon, such as a silicon wafer having an overlying $SiO_2$ coating, the layer thickness can be measured in a nondestructive manner using the technique described in our paper "Resonant Frustrated Total Reflection Technique for the Characterization of Thin Films" published in *Applied Optics*, Vol. 21, No. 12, June 15, 1982 at pages 2167–2173 herein incorporated by reference. N. J. Harrick, in his book *Internal Reflection Spectroscopy*, Interscience Publishers (1971) at pages 41–61 and in two papers "Total Internal Reflection", *Annals*, New York Academy of Science (1963) at pages 929, 948–949 and "Studies of Physics and Chemistry of Surfaces from Frustrated Total Internal Reflections", *Physical Review Letters*, Vol. 4, No. 5, Mar. 1960, at pages 224–226 (herein incorporated by reference) also describe a technique for nondestructively characterizing single layer structures.

To characterize a single layer structure using the principles of frustrated total reflection (FTR), an optical coupler is placed in contact with the thin film layer. In practice, the coupler comprises a hemicylinder having a flat base which is pressed against the thin film layer. Because of surface imperfections, there will typically be a gap or layer of air between the base of the coupler and the surface of the thin film layer.

A beam of collimated electromagnetic radiation is directed into the coupler at such an angle so that the radiation strikes the base and is reflected therefrom. Because of the hemicylindrical geometry of the coupler, the radiation reflected from its base will, upon striking the curved suface of the coupler, be normal thereto and pass readily therethrough. Notwithstanding the reflection of the beam from the base of the coupler, a portion of the energy of the beam is nonetheless coupled into the thin film layer via an imaginary wave of exponentially decreasing amplitude (an evanescent wave) which exits in the layer of air separating the coupler from the thin film layer. Within the thin film layer, the wave ceases to exponentially decay, that is, it ceases to evanesce. The wave becomes real, that is, substantially fixed in amplitude. This beam which propagates through the thin film layer is reflected at the thin film-layer substrate interface and is then reflected at the air-thin film interface.

As the beam propagates through the thin-film layer, the beam undergoes a shift in phase. The magnitude of the phase shift of the wave varies as the magnitude of the expression $(n_f t_f \cos\theta)/\lambda$ where $n_f$ and $t_f$ are the index of refraction and the thickness, respectively, of the thin film layer, $\theta$ is the angle at which the beam enters the coupler and $\lambda$ is the wavelength of the beam. Thus, the magnitude of the shift in phase of the beam is proportional to the thickness of the thin film layer. For a thin film layer of a certain thickness there is a certain phase shift of the beam associated therewith. The magnitude of the phase shift of the beam as it propagates through the thin film layer is often referred to as the "phase thickness" of the layer.

By scanning the coupler with the beam either by varying $\lambda$ or $\theta$ or both, the phase thickness of the thin film layer can be varied. When the phase thickness of the thin film layer equals the sum of the shift in phase which the beam undergoes at the interface between the layer of air and thin film layer and at the interface between the thin film layer and the substrate, then resonance will occur. At resonance, little of the energy of the beam propagating through the thin film layer and reflected at the thin film layer-air layer interface is coupled back into the coupler through the air layer for combination with the beam reflected from the coupler because of interference. As a result, for those values of $\lambda$ and $\theta$ at which resonance occurs, sharp minima appear in the spectra of the intensity of the radiation reflected from the optical coupler. From a knowledge of the value of $\lambda$ and $\theta$ at which resonance occurs, the theoretical thickness of the thin film layer can be calculated. In practice, the error between the theoretical thickness and the actual layer thickness has been found to be quite small.

In addition to enabling nondestructive measurement of the layer thickness, the FTR technique described in our paper can also be used to determine the index of refraction $n_f$ of the single thin film layer at various locations thereon to determine the homogeneity thereof. If both the thickness and index of refraction of the layer are unknown, then for two sets of values of $\lambda$ and $\theta$ at which resonance occurs, two equations relating index of refraction and layer thickness can be obtained. From the two equations, a value for the index of refraction and for the layer thickness can be obtained. Since the index of refraction of the thin film layer is indicative of its composition, by measuring the index of refraction at several locations thereon, the homogeneity of the layer can be determined.

The FTR layer characterization technique is most effective for determining characteristics of a single layer. However, problems arise when attempts are made to measure the thickness and the index of refraction of the individual layers of a multilayer thin film structure, such as an integrated circuit device. One reason why the previously described method is unsuited for characterizing the individual layers of a multilayer thin film structure is that the technique fails to account for the individual phase thickness associated with each layer. A further reason is that the prior technique does not take into account the fact that when a beam propagates through a multilayer thin film structure it is partially reflected and partially transmitted at the interface between each pair of layers. Accordingly, characterization of the layers of a multilayer thin film structure in the past has been accomplished by viewing a cross section thereof under a scanning electron microscope with the disadvantages attendant thereto.

Thus, there is a need for a technique for nondestructively characterizing the individual layers of a multilayer thin film structure.

SUMMARY OF THE INVENTION

The foregoing problems are overcome by the method of the present invention for nondestructively determining the characteristics of each layer of a multilayer thin film structure. The method is initiated by directing a first beam of radiation into an optical coupler, having a base in contact with the surface of a multilayer thin film structure, at such an angle that the beam is reflected therefrom with an evanescent wave component passing from the coupler and coupling into the multilayer thin film structure as a real beam. The real beam is reflected from the layers of the multilayer thin film structure back into the coupler where it combines with the beam of radiation reflected from the base. The combined beams exit the coupler with an intensity related to the characteristics of the structure layers. The coupler is scanned by the first beam during which time the reflectance intensity of combined beams leaving the coupler is measured. The detected reflectance intensity is then compared to the reflectance intensity of structures having known characteristics to determine the characteristics of the multilayer thin film structure.

DETAILED DESCRIPTION

Figure 1:
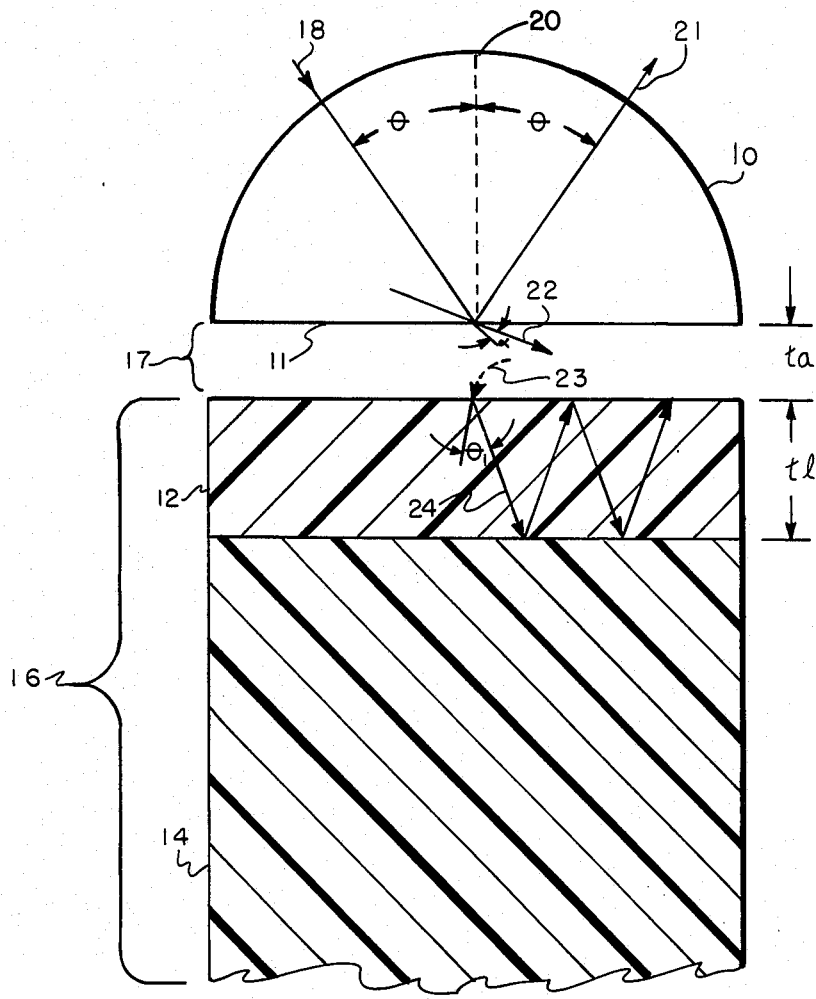
FIG. 1 is a cross-sectional view in elevation of an optical coupler in contact with a single layer thin film structure.

FIG. 1 shows an optical coupler 10 which takes the form of a hemicylinder having a flat base 11 thereon extending axially therealong. The base 11 of the hemicylinder 10 is placed in contact with a substantially transparent thin film layer 12 of a thickness $t_f$ (typically 1–10 $\mu$m) on the upper surface of substrate 14 which is energy absorptive. The film 12 and the substrate 14 together comprise a single layer thin film structure 16.

In practice, there are imperfections in the base 11 of the coupler 10 and in the thin film layer 12 so that when they are placed in contact with each other, there will be at least one gap or layer of air 17 present therebetween. In practice, the layer 17 has a thickness $t_a$ of 0.1–0.2 $\mu$m and like the thickness $t_f$ of layer 12, has been greatly exaggerated in FIG. 1 for purposes of illustration.

A beam of collimated radiation 18 from a source such as a laser (not shown) of a wavelength $\lambda$ is directed into the coupler 10 at an angle $\theta$ with respect to a line 20 passing radially through the coupler so as to be normal to the base 11. A portion of the incident beam 18 striking the coupler 10 is reflected at the base 11 and is depicted as beam 21. Because of the hemicylindrical geometry of the coupler 10, the reflected beam 21, upon striking the curved surface of the coupler, will be normal thereto. As a result, the reflected beam 21 passes from the coupler 10 into free space.

Another portion of the incident beam 18 striking the coupler is refracted thereby and passes from the base 11 into the air layer 17. The refracted beam is identified by reference numeral 22. The refracted beam 22 makes an angle $\alpha$ with the line 20 which, from Snell's Law, is given by $$n_c \sin\theta = n_a \sin\alpha \tag{1}$$

where $n_c$ and $n_a$ are the indices of refraction of the coupler 10 and the layer 17, respectively. In practice, $n_a$ is assumed to be 1.0. For purposes of simplicity, the coupler 10 is assumed to be transparent. Therefore, the index of refraction $n_c$ of the coupler 10 is assumed to be a real value rather than a complex value as would be the case if account was taken of the impurities in the coupler which could cause some absorption of the light passing therethrough.

If the index of refraction $n_c$ of the coupler 10 is greater than $n_a$, then at a critical angle $\theta_c$ the angle $\alpha$ becomes 90°. The critical angle $\theta_c$ is mathematically defined by the relationship $$\sin\theta_c = n_a/n_c \tag{2}$$

The critical angle $\theta_c$ depends on the index of refraction $n_c$ of the coupler 10. For example, when the coupler 10 is fabricated from germanium which has an index of refraction of $n_c = 4.0$, then $\theta_c$ is approximately 15°.

For the condition $\theta = \theta_c$, at which the angle $\alpha$ of the refracted beam 22 becomes 90°, the beam 18 incident on the coupler 10 appears to be totally reflected from the base 11 for the condition when no thin film layer 12 is in contact with the base. However, when the thin film layer 12 is in contact with the base 11 and $\theta > \theta_c$, then the refracted beam 22 no longer remains real because the angle of refraction $\alpha$ now possesses both a real and imaginary component in order for equation (1) to remain satisfied. As a consequence of the imaginary component in the angle $\alpha$, the radiation coupled by the coupler 10 into the layer 17 propagates therethrough not as beam 22 which is real, but as an imaginary wave 23 which decays exponentially (evanesces).

The evanescent wave 23, when it enters the interface between the layer 17 of air and the thin film layer 12, ceases to be imaginary. Upon entering the layer 12, the evanescent wave 23 becomes a real beam 24. The transformation of the evanescent wave 23 into the real beam 24 occurs because, when the index of refraction of thin film layer 12 is greater than $n_a$, then the angle $\theta_1$ at which radiation propagates through the thin film layer 12 has no imaginary component. Hence, any radiation which propagates through the thin film layer 12 will not be imaginary but will appear as a real beam. The value of $\theta_1$ can be obtained from the value of $\theta$ using equation (1).

Upon striking the substrate 14, the beam 24 is partially reflected therefrom and partially transmitted therethrough. However, since the substrate 14 is typically energy absorptive, that portion of the beam 24 propagating therethrough is absorbed thereby. The portion of the beam 24 reflected by the substrate 14 propagates back through the thin film layer 12, and when $\theta > \theta_c$, the beam will be internally reflected at the layer 17—thin film layer 12 interface in the same manner the beam 18 is reflected from the coupler 10. However, some radiation will be coupled back through the layer 17 of air and into the coupler 10 by way of an evanescent wave (not shown) in exactly the same way that radiation is coupled into the thin film layer 12 by the evanescent wave 23.

The beam 24 propagating through the layer 12 undergoes a shift in phase, the magnitude of which is dependent on a quantity associated with the thin film layer known as phase thickness $\psi$. Mathematically, the phase thickness $\psi$ of the thin film layer 12 is given by the expression $$\psi = (2\pi n_f t_f \cos\theta_1)/\lambda \tag{3}$$

where $n_f$ is the index of refraction of the thin film layer. In practice, the wavelength of the beam 18 of entering the coupler 10 is selected such that the thin film layer 12 appears transparent to the beam 24 which propagates therethrough. Thus the index of refraction $n_f$ of the thin film layer 12 is assumed to take on a real, rather than complex value.

By varying the angle $\theta$ at which the beam 18 enters the coupler 10 or by varying the wavelength $\lambda$ thereof, while holding the other parameter constant, the phase thickness of the thin layer 12 can be made to vary. In practice, the angle $\theta$ is made to vary while $\lambda$ is held constant. For one or more values of $\theta$ and $\lambda$, the shift in phase of the beam 24 attributable to the phase thickness of the thin film layer 12 will equal the sum of the phase shift of the beam at the interface between the layer 17 and layer 12 and at the interface between the layer 12 and the substrate 14. Mathematically, such a condition may be expressed by $$2\psi - \phi_{17,12} - \phi_{12,14} = 0 \ (\text{mod } 2\pi) \tag{4}$$

where $\phi_{17,12}$ and $\phi_{12,14}$ represent the angular phase shift of the beam 24 at the interface between the layer 17 of air and the thin film layer 12 and at the interface between the thin film layer and the substrate 14, respectively.

The phase shift $\phi_{17,12}$ is given by the expression $$\text{Tan}\left(\frac{\phi_{17,12}}{2}\right) = \left(\frac{\text{Sin}^2\theta_1 - (n_a/n_f)^2}{\cos\theta_1}\right)^{\frac{1}{2}} \tag{5}$$

The phase shift $\phi_{14,16}$ is given by a similar expression $$\text{Tan}\left(\frac{\phi_{12,14}}{2}\right) = \left(\frac{\text{Sin}^2\theta_1 - (n_f/N_s)^2}{\cos\theta_1}\right)^{\frac{1}{2}} \tag{6}$$

Since the substrate 14 is energy absorptive its index of refraction $N_s$ will be given by the expression $n_s - iK_s$ where $n_s$ is the real component and $K_s$ is the imaginary component, representing the absorption of energy by the substrate.

For those values of $\lambda$ and $\theta$ at which equation (4) is satisfied, a condition of resonance exists. At resonance, very little, if any, energy is coupled from the thin film layer 12 back into the layer 17 via an evanescent wave because of destructive interference which occurs each time the beam 24 is reflected at the thin film layer 12 - layer 17 interface. As a result, at resonance, there will be a sharp decrease in the measured intensity of the reflected beam 21 since practically very little of the beam 24 is coupled back into the coupler 10 to combine with the reflected beam.

Figure 2:
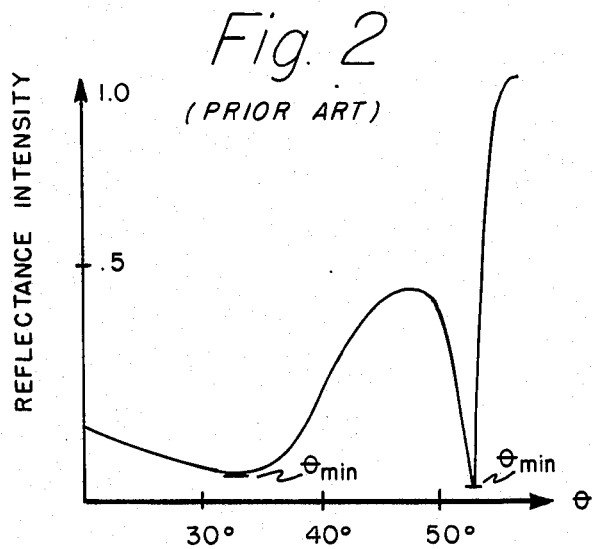
FIG. 2 is a graphical representation of the reflectance spectra associated with the single layer thin film structure of FIG. 1.

The thin film structure 16 has a particular reflectance spectra associated herewith, illustrated in FIG. 2, which is obtained by plotting the intensity of the reflected beam 21 as a function $\theta$. The value of $\theta$ associated with each minima in the spectra, designated as $\theta_{min}$, corresponds to the value of $\theta$ at each condition of resonance. From the value of $\theta_{min}$ obtained from the reflectance spectra of FIG. 2, the theoretical thickness $t_l$ of the layer 12 can be calculated using equations (3) and (4). In practice, very good agreement has been found between the actual layer thickness, as measured by using an electron scanning microscope, and the theoretical layer thickness.

Figure 3:
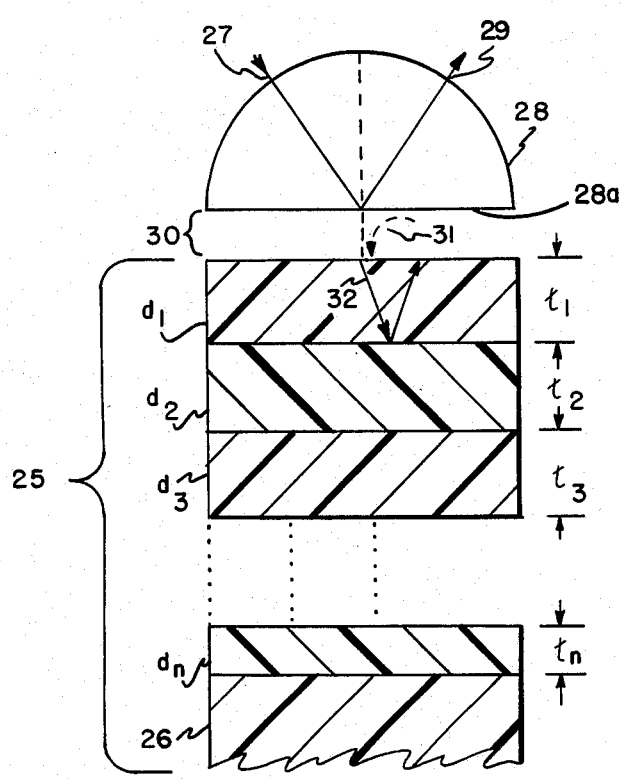
FIG. 3 is a cross-sectional view in elevation of an optical coupler in contact with the top surface of a multilayer thin film structure.

Referring to FIG. 3, the above-described FTR technique has not proven useful for characterizing the layer thickness and homogeneity of a multilayer thin film structure 25, comprised of an energy absorbing substrate 26 overlying which is a plurality of thin film layers $d_1, d_2, d_3 \ldots d_n$, each having a thickness $t_1, t_2, t_3 \ldots t_n$, respectively, and an index of refraction $n_1, n_2, n_3 \ldots n_n$, respectively. The reason why difficulties arise in attempting to use the previously-described FTR technique for characterizing the multilayer thin film structure 25 will become clear from an explanation of what happens when a beam 27 of radiation from a laser (not shown) is directed into a hemicylindrical optical coupler 28 whose flat base 28a is placed on the layer $d_1$ on the thin film structure 25. Because of surface imperfections in the base 28a of the coupler 28 and the layer $d_1$, a gap or layer 30 of air (typically 0.1–0.2 μm) will be present therebetween.

If the beam 27 enters the coupler 28 at an angle $\theta$ greater than the critical angle $\theta_c$, then the beam is reflected from the base 28a and will pass from the coupler because of the geometry thereof. The reflected beam is identified by reference numeral 29. Notwithstanding the reflection of the incident beam 27 at the base 28a of the coupler 28, a portion of the radiation of the incident beam is coupled into the layer $d_1$ by an evanescent wave 31. The wave 31 is coupled into the layer of air 30 in exactly the same manner that a portion of the radiation of the beam 18 of FIG. 1 is coupled into layer 12 of FIG. 1 by the evanescent wave 23. Upon entering the layer $d_1$, the wave 31 is transformed into a real beam 32. The transformation of the evanescent wave 31 in the real beam 32 occurs because the index of refraction $n_1$ of the layer $d_1$ typically exceeds the index of refraction $n_a$ of the layer 30 of air. Thus, the angle (not shown) at which the radiation propagates through the layer $d_1$ has no imaginary component so the radiation propagates as the real beam 32 rather than the evanescent wave 31. Note that the beam 32 may be transformed into an evanescent wave within one or more of the layers $d_2, d_3 \ldots d_n$ depending on the relationship of the indices of refraction of each pair of adjacent layers.

As the beam 32 propagates through each of the layers $d_1$–$d_n$, the beam undergoes a shift in phase depending on the phase thickness of each layer. At the interface between layers, a portion of the beam 32 is reflected, while the remaining portion is transmitted into the next layer. The prior art FTR technique fails to account for both the phase shift of the beam 32 through each layer and the partial reflection and transmission of the beam at the interface between layers. Thus the prior art FTR technique is unsuited for characterizing the multilayer thin film structure 25.

Figure 4:
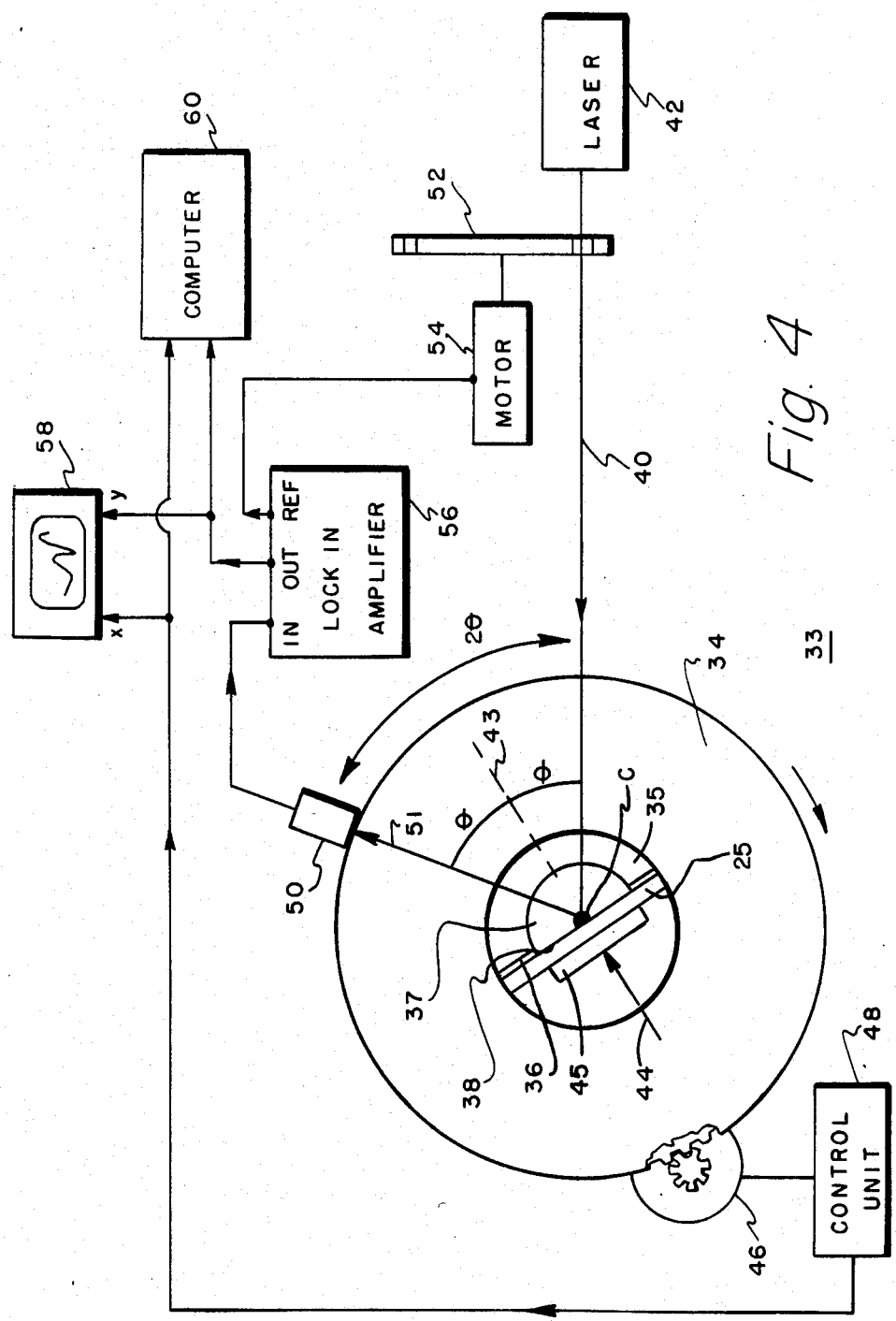
FIG. 4 is a schematic diagram of an apparatus according to the present invention for nondestructively characterizing the layers of the multilayer thin film structure of FIG. 3.

Referring to FIG. 4, there is shown a block schematic diagram of a measurement system 33 for nondestructively characterizing the individual layers $d_1$–$d_n$ of the multilayer thin film structure 25 of FIG. 3 and particularly for determining the thickness $t_1$–$t_n$, respectively, thereof using the principles of frustrated total reflectance (FTR). The measurement system 33 comprises a rotatable table 34 which has an upstanding support member 35 thereon whose upper portion is hemicylindrical. The hemicylindrical portion of support member 35 has a flat surface 36 thereon which is provided with a recess for receiving a hemicylindrical coupler 37. The coupler 37 has a flat base 38 which typically protrudes slightly beyond the surface 36 on the support member 35 for intimately contacting the top surface of the multilayer thin film structure 25. In seating the coupler 37 in the recess in the surface 36 of the support member 35, the center c of the coupler must be aligned with the center of the table. In this way, when a beam 40 of radiation, produced by a laser 42, is directed into the coupler 37 at an angle $\theta$ measured with respect to a line 43 perpendicular to the base 38 of the coupler 37, the beam impinges at the same spot along the interface between the base and the multilayer thin film structure 25 as the table 34 is rotated. In practice, the wavelength $\lambda$ of the beam 40 is selected such that each of the layers $d_1$–$d_n$ appears transparent thereto.

The multilayer thin film structure 25 of FIG. 3 is held parallel to, and in contact with, the base 38 on the coupler 37 of FIG. 4 by directing compressed air, represented by arrow 44, against a block 45 in intimate contact with the bottom surface of the multilayer thin film structure.

The table 34 is rotatably driven by a servo motor 46, to a precision of 0.005°, under the control of a control unit 48 causing the coupler 37 to be scanned by the beam 40 at various angles greater than $\theta_c$. In practice, the servo motor 46 and the control unit 48 comprise a model 35-2500 servo motor and model 35-2450 control unit, respectively, manufactured by the Ealing Corporation of South Natick, Mass.

The servo motor 46 also rotatably drives a pyroelectric type photodetector 50 about the table 34 through a gear box (not shown) so that the photodetector rotates in the same direction as the table at a speed twice as fast. By rotatably driving the photodetector 50 at a speed twice the rotational speed of the table 34, the angle between the photodetector and the beam 40 incident on the coupler 36 is maintained at 2$\theta$. This assures that the portion of the beam 40 reflected by the coupler 36 (identified as reflected beam 51) is always centered on the detector 50 as the table 34 is rotated.

In practice, there is usually some spurious electromagnetic radiation (noise) present in the beam 40 which may detrimentally effect the measurement of the intensity of the beam 51 by the photodetector 50. The detrimental effect of the noise in the beam 51 can be reduced by modulating the beam 40 and synchronizing the output signal of the detector 50 thereto. Further, in practice, since the detector 50 is of the pyroelectric variety the beam 51 incident thereon must be time-modulated in order for the detector to operate properly. To this end, a circular shutter plate 52 is interposed between the laser 42 and the coupler 37. The shutter plate 52 is rotatably driven by a motor 54 responsive to a fixed frequency reference signal produced by a lock-in amplifier 56 at its reference signal output. Typically, the amplifier 56 comprises a model 124A amplifier manufactured by Princeton Applied Research Co. of Princeton, N.J.

The lock-in amplifier 56 has an input coupled to the output of the photodetector 50. Those signals at the input of the lock-in amplifier 56 which are approximately equal in frequency to the reference signal supplied to the motor 54 are amplified by the amplifier and passed to its output. Those signals whose frequency is larger or smaller than that of the fixed frequency reference signal are rejected by the lock-in amplifier 56.

By amplifying only those signals from the photodetector 50 which are approximately equal in frequency to the reference signal supplied to the motor 54, the lock-in amplifier 56 effectively synchronizes the output signal of the photodetector 50 to the modulation of the beam 51 which is identical to the modulation of beam 40. By synchronizing the output signal of the photodetector 50 to the modulation of the beam 40, the amplitude of the output signal of the detector is made much less sensitive to any noise in the beam.

In practice, an X-Y cathode ray tube (CRT) display apparatus 58 has a Y input coupled to the output of the lock-in amplifier 56. The CRT display device 58 has an X input coupled to the control unit 48 so as to be supplied therefrom with periodic pulses, the frequency of which vary as the rotational speed of the table 34. The CRT display device 58 will display a waveform which corresponds to the variation in the output signal amplitude of the detector 50 as a function of the rotation of the table 34. Thus, the resultant waveform displayed on the CRT display 58 corresponds to the reflectance spectra associated with the thin film structure 25.

The output signal of the control unit 48 and the output signal of the lock-in amplifier 56 are also supplied to a first and second input of a computer 60, typically comprising a model MINC-23 computer manufactured by Digital Equipment Corporation, Maynard, Mass. The computer 60 contains a program, illustrated in flow chart form in FIG. 5, which, when executed, determines the thicknesses $t_1-t_n$ of the layers $d_1-d_n$, respectively, of the multilayer thin film structure 24 of FIG. 3.

Figure 5:
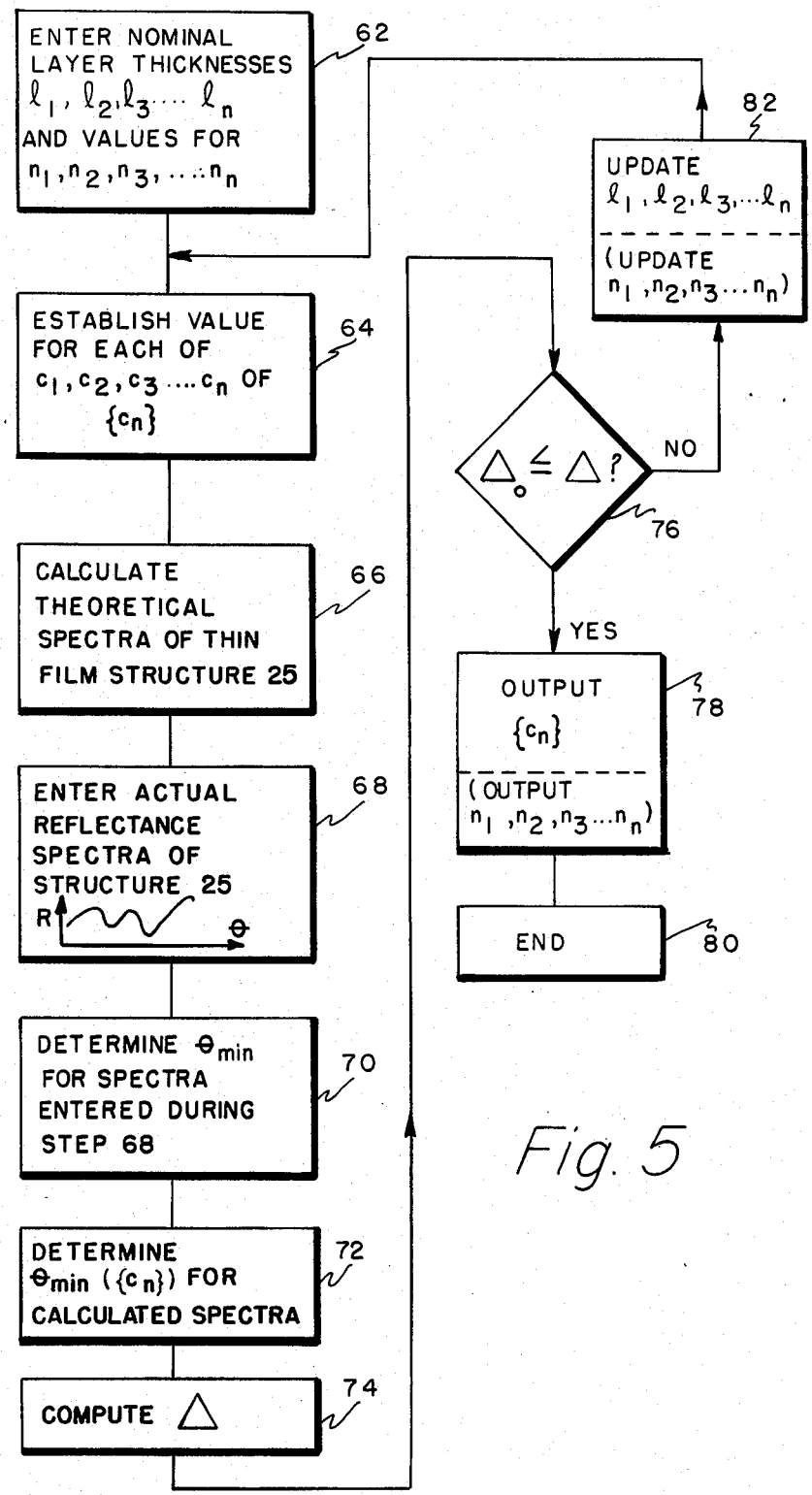
FIG. 5 is a flow chart representation of the program executed by the apparatus of FIG. 4 to characterize the multilayer thin film structure of FIG. 3.

Referring to FIG. 5, program execution is initiated by entering a set of values $l_1, l_2, l_3 \ldots l_n$ each representing the nominal thickness of a corresponding one of the layers of $d_1, d_2, d_3 \ldots d_n$, respectively, of the thin film structure 25 of FIG. 3 (step 62). In practice, the nominal thickness of each layer is approximated from the expected thickness thereof based on the design of the thin film structure 25. In the event that the nominal thickness of each of the layers $d_1-d_n$ cannot be approximated, arbitrary values may be entered for $l_1, l_2, l_3 \ldots l_n$.

During step 62, values for $n_1, n_2, n_3 \ldots n_n$, each representing the index of refraction of the corresponding one of the layers $d_1-d_n$, respectively, are also entered. Typically, each of layers $d_1-d_n$ is assumed to be transparent so that the refractive indices $n_1-n_n$ of the layers $d_1-d_n$, respectively, are entered as real, rather than complex values. However, in certain instances such as when the structure 25 possesses a very small number of layers, it may become necessary to actually account for the small but finite amount of absorption of radiation by each layer so that complex values must be entered for each of $n_1, n_2, n_3 \ldots n_n$.

Following step 62, each of the components $c_1, c_2, c_3 \ldots c_n$ of a vector $\{c_n\}$ is assigned the value of a separate one of the previously entered nominal thickness values $l_1, l_2, l_3 \ldots l_n$, respectively (step 64). Next, the theoretical reflectance spectra of the structure 25 as a function of the angle $\theta$ is calculated in accordance with the vector $\{c_n\}$ (step 66).

To accurately compute the theoretical reflectance spectra associated with the structure 25 during step 66, it is necessary to account for the fact that the beam 32 of FIG. 3 propagating through the multilayer thin film structure 25 of FIG. 3 is partially transmitted and partially reflected upon striking the interface between a pair of layers $d_{i-1}$ and $d_i (i \leq n)$. The partial reflection and partial transmission of the wave 32 of FIG. 3 at the interface between layers $d_{i-1}$, $d_i$ can be mathematically expressed by a matrix $\overleftrightarrow{T}_{i-1,i}$ $$\overleftrightarrow{T}_{i-1,i} = \frac{1}{tr_{i-1,i}} \begin{vmatrix} 1 & r_{i-1,i} \\ r_{i-1,i} & 1 \end{vmatrix} \quad (7)$$

The terms $tr_{i-1,i}$ and $r_{i-1,i}$ represent the transmission and reflection coefficients of the beam 32, respectively, at the interface between the two layers. The reflection coefficient $r_{i-1,i}$ is given by the expression $$r_{i-1,i} = \frac{(n_{i-1}/n_i) - 1}{(n_{i-1}/n_i) + 1} \quad (8)$$

where $n_{i-1}$ and $n_i$ are the indices of refraction of the layers $d_{i-1}$ and $d_i$, respectively. The transmission coefficient $tr_{i-1,i}$ is given by the expression $$tr_{i-1,i} = \frac{2}{(n_{i-1}/n_i) + 1} \quad (9)$$

In order to accurately compute the reflectance spectra of the multilayer thin film structure 25, it is also necessary to account for the fact that there is a phase thickness associated with each layer $d_i$. Mathematically, the phase thickness of each layer di can be expressed by a matrix $\overleftrightarrow{\psi}_i$ $$\overleftrightarrow{\psi}_i = \begin{vmatrix} e^{j\beta i} & 0 \\ 0 & e^{-j\beta i} \end{vmatrix} \quad (10)$$

where j is the complex operator and $\beta_i$ is given by the expression $$\beta_i = 2\pi/\lambda \cos(\theta_i) d_i n_i \quad (11)$$

where $\theta_i$ represents the angle between the beam traveling through the layer $d_i$ and a line (not shown) normal to the interface between the layers $d_{i-1}$ and $d_i$. The value of $\theta_i$ is obtained from the value of $\theta_{i-1}$ using Snell's Law. A value for $\theta_1$ is obtained from $\theta$ using Snell's Law.

The multilayer thin film structure 25 may be thought of as an ordered sequence of layers with an associated interface therebetween. Mathematically, the structure 25 can be characterized by $2\times 2$ matrix $\vec{S}$ which is the ordered product of the matrices $\vec{I}_{1,2}, \vec{I}_{2,3} \ldots \vec{I}_{n-1,n}$ and the matrices $\vec{\psi}_1, \vec{\psi}_2, \vec{\psi}_3 \ldots \vec{\psi}_n$. Mathematically, the matrix S can be expressed as $$\vec{S} = \begin{vmatrix} S_{11} & S_{12} \\ S_{21} & S_{22} \end{vmatrix} = I_{0,1} \cdot \psi_1 I_{1,2} \cdot \psi_2 \ldots I_{n-1,n} \psi_n \quad (12)$$

Once the matrix S has been found, the intensity R of the light reflected from the coupler 36 for each value $\theta$ will be given by $[S_{21}/S_{11}]^2$. Note that for each new value of $\theta$, the matrix S must be recomputed. By computing the intensity R for each of a plurality of values of $\theta$, the theoretical reflectance spectra for the structure 25 is obtained.

Following calculation of the theoretical reflectance spectra associated with the multilayer thin film structure 25, the actual reflectance spectra associated therewith is entered into computer 60 of FIG. 4 during step 68 of FIG. 5. The computer 60 enters the actual reflectance spectra by reading the magnitude of the output signal of the lock-in amplifier 56 (FIG. 4) each time a pulse is produced at the output of the control unit 48 of FIG. 4.

Once the actual spectra has been entered, the computer 60 determines each of the angular minima ($\theta_{min}$) which are present in the actual reflectance spectra of the multilayer thin film structure 25 (step 70). The computer 60 then determines each of the angular minima ($\theta_{min}\{c_n\}$) present in the theoretical reflectance spectra associated with the multilayer thin film structure 25 (step 72).

Once each of $\theta_{min}$ and $\theta_{min}(\{c_n\})$ have been determined, a difference value, $\Delta$, is calculated (step 74) in accordance with the relationship $$\Delta = \Sigma[\theta_{min} - \theta_{min}(\{c_n\})]^2 \quad (13)$$

Thereafter, the value of $\Delta$ is compared to a predetermined measurement tolerance value $\Delta_o$ (step 76). When $\Delta_0 \geq \Delta$ then, the value of the components $c_1, c_2 \ldots c_n$ of the vector $\{c_n\}$ are considered to accurately approximate the actual layer thicknesses $t_1, t_2, t_3 \ldots t_n$ of the layers of $d_1, d_2, d_3 \ldots d_n$, respectively. Therefore, if the condition $\Delta_0 \geq \Delta$ is satisfied during the execution of step 76, then, program execution thereafter branches to step 78 whereupon the computer 60 outputs the vector $\{c_n\}$, the components of which accurately approximate the layer thickness $t_1, t_2, t_3 \ldots t_n$, respectively. Following step 78 program execution ends (step 80).

In the event that the difference value $\Delta$ calculated during step 74 is greater than the predetermined tolerance value $\Delta_0$, then following step 76, program execution branches to step 82 whereupon the nominal thickness values $l_1, l_2, l_3 \ldots l_n$ are updated. The current value of each of the nominal thicknesses $l_1, l_2, l_3 \ldots l_n$ is replaced with a new value computed in accordance with the value of the derivative of the difference between $\Delta$ and $\Delta_0$. Following step 82, program execution branches to step 64 during which the value of each of the components $c_1, c_2, c_3 \ldots c_n$ of the vector $\{c_n\}$ is set equal to the corresponding one of the newly updated nominal thickness values $l_1, l_3 \ldots l_n$, respectively. After step 64, steps 66-74 are reexecuted to determine the difference $\Delta$ between $\theta_{min}$ and $\theta_{min}(\{c_n\})$.

Once a new value $\Delta$ has been calculated during the subsequent execution of step 74, this value of $\Delta$ is compared to $\Delta_0$ during step 76. Should $\Delta$ be greater than $\Delta_o$ during reexecution of step 76, the program execution branches to step 82 during which the previously updated nominal layer thickness values $l_1, l_2, l_3$ are again updated before proceeding once again to step 64. Otherwise, should $\Delta_o$ be greater than $\Delta$ during step 76, then program execution will branch to step 78.

The number of iterations of the program required to obtain an accurate approximation of the layer thicknesses $t_1, t_2, t_3 \ldots t_n$ depends on how closely the nominal layer thickness values $l_1, l_2, l_3 \ldots l_n$ entered during step 62 approximate the actual layer thickness values. If the nominal layer thickness values entered during step 62 do not differ very much from the actual layer thicknesses of the multilayer thin film structure 24, then only a few iterations of the program may be necessary.

As may now be appreciated, the above-described program operates to determine the layer thickness $t_1-t_n$ of layers $d_1-d_n$, respectively, by comparing the actual reflectance spectra associated with the structure 25 to the reflectance spectra of multilayer thin film structures having known characteristics until a substantial match between reflectance spectra is obtained. Instead of calculating the reflectance spectra of the different multilayer thin film structures in the manner described above, the actual reflectance spectra of each could be measured.

In addition to determining the layer thickness $t_1, t_2, t_3 \ldots t_n$ of the layers $d_1, d_2, d_3 \ldots d_n$, respectively, of the thin film structure 25 of FIG. 3, the program of FIG. 5 can also determine the index of refraction of $n_1, n_2, n_3 \ldots n_n$ of each of the layers, respectively, as well. During step 62, nominal values of $n_1, n_2, n_3 \ldots n_n$ are entered together with the nominal thickness values $l_1, l_2, l_3 \ldots l_n$. Program execution of steps 64-76 then proceed in the manner described previously with the nominal values of $n_1-n_n$ being used to compute each $\theta_{min}(\{c_n\})$.

If $\Delta_o \leq \Delta$ when these two terms are compared during step 76, then during step 82, not only are the values of $l_1, l_2, l_3 \ldots l_n$ updated, but the values of $n_1, n_2, n_3$ are updated as well. When the condition $\Delta_o \geq \Delta$ is satisfied during subsequent reexecution step 76, then each of the values of $n_1, n_2, n_3 \ldots n_n$ entered during step 62 (and updated as necessary during one or more executions of step 82) is output during step 78 as being an accurate approximation of the actual refractive index of a corresponding one of the layers $d_1, d_2, d_3 \ldots d_n$, respectively.

Determination of the index of refraction $n_1, n_2, n_3 \ldots n_n$ of the layers $d_1, d_2, d_3 \ldots d_n$ allows the composition of each layer to be established since a particular layer composition has a specific index of refraction associated therewith. By determining the index of refraction of each layer at various locations thereon, the FTR characterization technique of the present invention enables homogeneity of the thin film structure 25 to be ascertained in a nondestructive manner.

Although the FTR technique of the present invention has been described for characterizing a structure having a plurality of discrete thin film layers, other structures such as a lightguide preform (not shown) whose media is more or less continuous, may also be characterized using this technique. A structure having a more or less continuous media can be characterized using the instant FTR technique by treating the structure as a multilayer thin film structure comprised of a plurality of imaginary layers, each of a uniform thickness but unknown composition. In other words, the index of refraction of each imaginary layer is treated as an unknown parameter.

Characterization of a continuous media structure is carried out in exactly the same fashion as described above for the discrete multilayer thin film structure 25 of FIG. 3 with one minor difference. Instead of updating the nominal layer thickness values $l_1, l_2, l_3 \ldots l_n$ during step 82 of FIG. 5, as occurs during characterization of the discrete multilayer thin film structure 25 of FIG. 3, the nominal layer thickness values remain constant during characterization of the continuous media structure. Only the values $n_1, n_2, n_3 \ldots n_n$, representing the index of refraction of each of the imaginary layers, are updated. From the updated values $n_1, n_2, n_3 \ldots n_n$, the index of refraction of each imaginary layer and the actual composition thereof can be accurately approximated.

It is to be understood that the embodiments described herein are merely illustrative of the principles of the invention. Various modifications may be made thereto by persons skilled in the art which will embody the principles of the invention and fall within the spirit and scope thereof.

What is claimed is:

1. A method for nondestructively characterizing the layers of a multilayer thin film structure, comprising the steps of:
    (a) directing a first beam of radiation into an optical coupler, having a base in contact with the surface of a multilayer thin film structure, at such an angle that the beam is reflected therefrom with an evanescent wave component passing from the coupler and coupling into the multilayer thin film structure as a real beam;
    (b) reflecting the real beam from the layers of the thin film structure back into the coupler where it combines with the beam of radiation reflected from the base and exits the coupler with an intensity related to the characteristics of the structure layers;
    (c) scanning the first beam into the coupler;
    (d) detecting the intensity of the combined beams exiting the coupler during the scanning of the first beam; and
    (e) comparing the detected reflectance intensity with the reflectance intensity of structures having known characteristics to determine the characteristics of the multilayer thin film structure.

2. The method according to claim 1 wherein the first beam is scanned into the coupler by varying the angle at which the beam enters the coupler.

3. The method according to claim 1 wherein said step of comparing the detected reflectance intensity with the reflectance intensity of structures having known characteristics comprises the steps of:
    determining the minima present in the detected reflectance intensity;
    determining the minima present in the reflectance intensity of the structures having known characteristics; and
    comparing the difference between the minima until a substantial match therebetween is obtained.

4. A method for nondestructively determining the individual thickness of each layer of a multilayer thin film structure comprising the steps of:
    (a) directing a first beam of radiation into an optical coupler having a flat base in contact with the top layer of the multilayer thin film structure at an angle such that the beam is reflected therefrom with an evanescent component passing from the coupler and coupling into the multilayer thin film structure as a real beam;
    (b) reflecting the real beam from the layers of the thin film structure back into the coupler where it combines with the beam reflected from the base and exits the coupler with an intensity related to the characteristics of the structure layers;
    (c) varying the angle at which the first beam enters the coupler;
    (d) detecting the intensity of the combined beams leaving the coupler as the angle of the first beam entering the coupler is varied to obtain the reflectance spectra associated with the multilayer thin film structure;
    (e) establishing a nominal thickness value for each layer of the structure;
    (f) computing the theoretical reflectance spectra associated with the multilayer thin film structure in accordance with the nominal layer thickness established therefor;
    (g) determining the angular minima present in both the detected reflectance spectra and the theoretical reflectance spectra associated with the multilayer thin film structure;
    (h) computing the difference $\Delta$ between the angular minima of the detected reflectance spectra and the angular minima of the theoretical reflectance spectra associated with the multilayer thin film structure; and
    (i) comparing the difference $\Delta$ to a predetermined tolerance value $\Delta_0$ and approximating the actual layer thickness from the established nominal layer thickness when $\Delta_0 \geq \Delta$, otherwise, establishing a new nominal thickness value for each layer and then repeating the steps (e), (f) and (g) before once again testing whether the condition $\Delta_0 \geq \Delta$.

5. Apparatus for nondestructively characterizing each layer of a multilayer thin film structure comprising:
    an optical coupler having a flat base in contact with the surface of a sample multilayer thin film structure;
    means for directing a first beam of radiation into the optical coupler at such an angle that the beam is totally reflected from the base with an evanescent wave component passing from the coupler and entering the multilayer thin film structure as a real beam which is reflected from the layers of the structure back into the coupler to combine with the beam reflected from the base and exit the coupler with an intensity related to the characteristics of the structure layers;

means for scanning the first beam into the coupler to vary the intensity of the radiation reflected from the layers of the structure; means for detecting the intensity of combined beams exiting tne optical coupler during scanning by the first beam; and means for comparing the detected reflectance intensity to the reflectance intensity of structures having known characteristics to determine the characteristics of the multilayer thin film structure.

6. The invention according to claim 5 wherein said means for directing the first beam of radiation into the optical coupler comprises a laser.

7. The invention according to claim 5 wherein said means for scanning the first beam into the coupler comprises means for rotating the coupler to vary the angle at which the beam of radiation enters the coupler.

8. The invention according to claim 7 wherein said means for detecting the intensity of the combined beams exiting the optical coupler comprises a photodetector mounted to said means for rotating the optical coupler so that said photodetector rotates in the same direction as the optical coupler at twice the speed.

9. The invention according to claim 5 wherein. said means for detecting the intensity of the combined beams exiting the optical coupler comprises a pyroelectric photodetector.

10. The invention according to claim 5 wherein said comparing means comprises a computer.

11. The invention according to claim 5 wherein said coupler comprises a hemicylinder having a flat base.

* * * * *